US011786360B2

(12) United States Patent
Graf et al.

(10) Patent No.: US 11,786,360 B2
(45) Date of Patent: Oct. 17, 2023

(54) ENCODED CINCHING MECHANISM FOR USE WITH AN IMPLANT DELIVERY SLEEVE

(71) Applicant: MENTOR WORLDWIDE LLC, Irvine, CA (US)

(72) Inventors: Udo Werner Graf, Goleta, CA (US); Robert J. Tannhauser, Bridgewater, NJ (US); Joseph Matton, Coto de Caza, CA (US); Leo B. Kriksunov, Ithaca, NY (US)

(73) Assignee: MENTOR WORLDWIDE LLC, Irvine, CA (US)

( * ) Notice: Subject to any disclaimer, the term of this patent is extended or adjusted under 35 U.S.C. 154(b) by 386 days.

(21) Appl. No.: 17/337,249

(22) Filed: Jun. 2, 2021

(65) Prior Publication Data
US 2022/0000604 A1   Jan. 6, 2022

Related U.S. Application Data

(60) Provisional application No. 63/046,917, filed on Jul. 1, 2020.

(51) Int. Cl.
*A61F 2/12* (2006.01)
(52) U.S. Cl.
CPC ........ *A61F 2/12* (2013.01); *A61F 2220/0075* (2013.01); *A61F 2220/0083* (2013.01); *A61F 2250/0089* (2013.01); *A61F 2250/0097* (2013.01)

(58) Field of Classification Search
CPC ................ A61F 2/12; A61F 2220/0075; A61F 2220/0083; A61F 2250/0089; A61F 2250/0097
See application file for complete search history.

(56) References Cited

U.S. PATENT DOCUMENTS

| | | | |
|---|---|---|---|
| 4,035,850 | A | 7/1977 | Cresswall |
| 4,955,906 | A | 9/1990 | Coggins et al. |
| 5,201,779 | A | 4/1993 | Shiao |
| 5,279,539 | A | 1/1994 | Bohan et al. |

(Continued)

FOREIGN PATENT DOCUMENTS

| | | |
|---|---|---|
| CN | 2897165 Y | 5/2007 |
| CN | 208552129 U | 3/2019 |

(Continued)

OTHER PUBLICATIONS

PCT Notification of Transmittal of the International Search Report and International Search Report of International Application No. PCT/IB2019/051820 dated Jun. 18, 2019, 8 Pages.

(Continued)

*Primary Examiner* — Suzette J Gherbi
(74) *Attorney, Agent, or Firm* — Etan S. Chatlynne; Calderon Safran & Cole P.C.

(57) ABSTRACT

The subject matter disclosed herein relates to an encoded cinching mechanism for use with an implant delivery sleeve. The delivery sleeve includes: an enclosure having a first portion, an orifice, and a throat disposed between the first portion and the orifice; and a cinching mechanism disposed about the throat, in which the cinching mechanism comprises a plurality of demarcations each of which are indicative of a sized opening of the throat.

19 Claims, 11 Drawing Sheets

(56) References Cited

U.S. PATENT DOCUMENTS

| | | | |
|---|---|---|---|
| 5,549,679 A | 8/1996 | Kuslich | |
| 5,723,006 A | 3/1998 | Edergerber | |
| 5,728,065 A | 3/1998 | Follmer et al. | |
| 6,467,612 B1* | 10/2002 | Rosenfeld | A61B 17/06123 |
| | | | 206/63.5 |
| 6,605,093 B1 | 8/2003 | Blake | |
| 8,070,768 B2* | 12/2011 | Kim | A61F 5/003 |
| | | | 606/198 |
| 8,182,459 B2 | 5/2012 | Dann et al. | |
| 8,187,297 B2* | 5/2012 | Makower | A61B 17/1285 |
| | | | 606/198 |
| 8,211,173 B2 | 7/2012 | Keller et al. | |
| 8,409,279 B2 | 4/2013 | Freund | |
| 8,641,758 B1 | 2/2014 | Anderson et al. | |
| 8,993,831 B2* | 3/2015 | Sharma | A61L 24/046 |
| | | | 514/772.3 |
| 9,414,941 B2 | 8/2016 | Placik et al. | |
| 10,105,213 B2 | 10/2018 | Weinzweig | |
| 10,842,602 B2* | 11/2020 | Alexander | A61L 27/14 |
| 11,324,581 B2* | 5/2022 | Heneveld | A61F 2/0095 |
| 11,452,511 B2* | 9/2022 | Barbot | A61B 17/00234 |
| 11,690,614 B2* | 7/2023 | Gross | A61B 17/06 |
| | | | 606/228 |
| 11,690,716 B2* | 7/2023 | Hosmer | A61F 2/2427 |
| | | | 623/2.11 |
| 11,712,345 B2* | 8/2023 | Olmos | A24D 1/00 |
| | | | 435/6.12 |
| 11,723,769 B2* | 8/2023 | Basude | A61F 2/246 |
| | | | 623/2.11 |
| 2002/0091443 A1 | 7/2002 | Yoon | |
| 2004/0225278 A1 | 11/2004 | Poole et al. | |
| 2005/0080430 A1 | 4/2005 | Wright, Jr. et al. | |
| 2007/0276484 A1 | 11/2007 | Abell et al. | |
| 2008/0167606 A1 | 7/2008 | Dann et al. | |
| 2009/0030400 A1 | 1/2009 | Bose et al. | |
| 2009/0204107 A1 | 8/2009 | Keller et al. | |
| 2011/0082546 A1* | 4/2011 | Freund | A61F 2/12 |
| | | | 623/8 |
| 2011/0144688 A1* | 6/2011 | Reiss | A61M 25/1002 |
| | | | 606/192 |
| 2014/0148901 A1 | 5/2014 | Anderson et al. | |
| 2014/0228951 A1 | 8/2014 | Zochowski | |
| 2014/0249510 A1 | 9/2014 | Koblish et al. | |
| 2014/0350462 A1 | 11/2014 | Ataollahi et al. | |
| 2015/0032208 A1 | 1/2015 | Preissman | |
| 2016/0095733 A1* | 4/2016 | Sharma | A61B 6/12 |
| | | | 606/198 |
| 2016/0374720 A1 | 12/2016 | Anderson et al. | |
| 2017/0007295 A1 | 1/2017 | Geisz | |
| 2017/0020500 A1 | 1/2017 | Taylor et al. | |
| 2017/0303905 A1 | 10/2017 | Wilson | |
| 2018/0116779 A1* | 5/2018 | Marx | A61F 2/0095 |
| 2018/0126119 A1 | 5/2018 | McNiven et al. | |
| 2019/0274817 A1* | 9/2019 | Hristov | A61B 17/3468 |
| 2019/0274818 A1 | 9/2019 | Hristov et al. | |
| 2019/0274819 A1 | 9/2019 | Graf | |
| 2019/0343620 A1* | 11/2019 | Mlodinow | A61F 2/12 |
| 2020/0222174 A1* | 7/2020 | Rosenberg | A61F 2/0059 |
| 2021/0052359 A1* | 2/2021 | Heneveld | A61F 2/0095 |
| 2021/0244527 A1* | 8/2021 | Heneveld | A61F 2/0095 |
| 2022/0054254 A1* | 2/2022 | Gryskiewicz | A61F 2/12 |
| 2022/0233297 A1* | 7/2022 | Heneveld | A61F 2/12 |
| 2023/0060747 A1* | 3/2023 | Marks | A61B 17/0401 |
| 2023/0098318 A1* | 3/2023 | Hristov | A61F 2/12 |
| | | | 606/1 |
| 2023/0255608 A1* | 8/2023 | Sarna | A61B 10/0291 |
| | | | 600/569 |

FOREIGN PATENT DOCUMENTS

| | | |
|---|---|---|
| EP | 2 630 927 A2 | 8/2013 |
| WO | 2010/126462 A1 | 11/2010 |
| WO | 2012/177587 A1 | 12/2012 |
| WO | 2017/213716 A1 | 12/2017 |
| WO | 2019/171300 A1 | 9/2019 |
| WO | 2010/099541 A1 | 9/2021 |

OTHER PUBLICATIONS

Shaa'ista Ameen, 'No Touch' Breast-Implant Insertion Device, Submitted To the University of Cape Town, Faculty of Health Sciences, Department of Human Biology, University of Cape Town, Date of Submission: Jan. 1, 2016, URL: https://open.uct.ac.za/bitstream/handle/11427/20491/thesis_hsf_2016_ameen_shaa_039_ista.pdf?sequene=1 [retrieved on Feb. 27, 2018], pp. 74-76.

PCT Notification of Transmittal of The International Search Report and the Written Opinion of the International Searching Authority, or the Declaration for International Application No. PCT/IB2021/055297 dated Oct. 4, 2021, 6 pages.

* cited by examiner

FIG. 12A  FIG. 13A  FIG. 14A
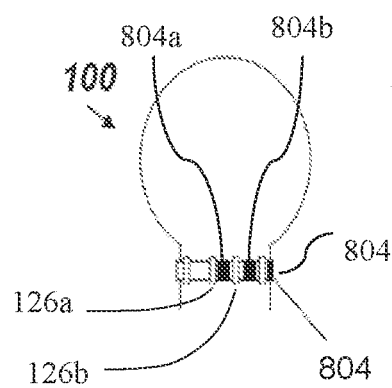
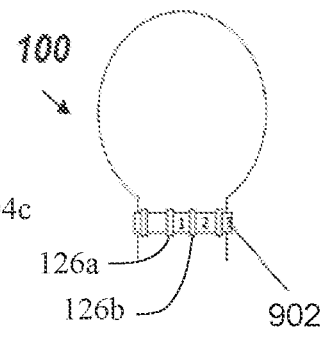
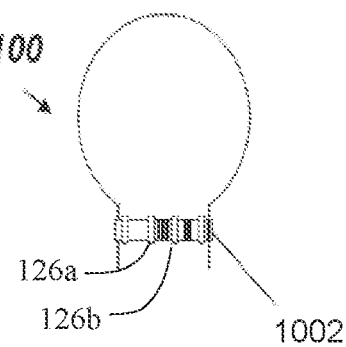
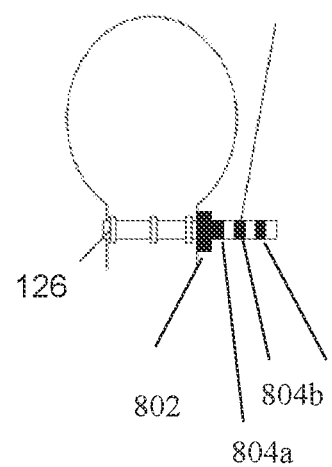
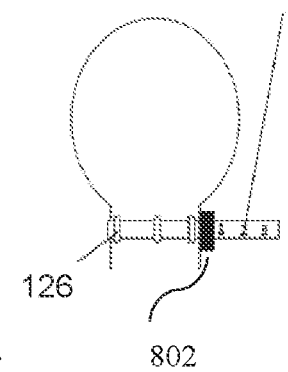
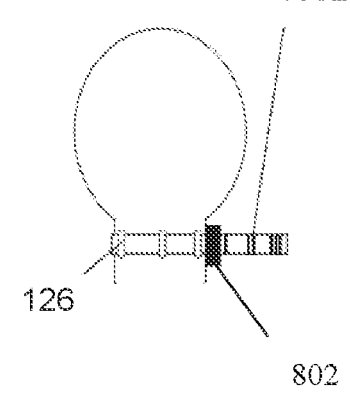
FIG. 12B  FIG. 13B  FIG. 14B

US 11,786,360 B2

ENCODED CINCHING MECHANISM FOR USE WITH AN IMPLANT DELIVERY SLEEVE

CROSS-REFERENCE TO CO-PENDING APPLICATION

The present application is claims priority under 35 U.S.C. § 119 to U.S. Provisional Patent Application No. 63/046,917, filed Jul. 1, 2020. The entire content of this application is incorporated by reference herein in its entirety.

FIELD

The subject matter disclosed herein relates to an encoded cinching mechanism for use with an implant delivery sleeve.

BACKGROUND

Flexible sleeves may be used as a delivery device for implanting a tissue implant, such as a silicone-gel breast implant, into a subject. These sleeves permit delivery of the implant through an incision that is shorter than it would need to be if the sleeve were not used. These sleeves may also lower the likelihood of introducing contaminants, e.g., microorganisms, into the subject through the incision because they minimize the amount of contact between the implant, surgeon's hands, and subject's tissue.

SUMMARY OF THE DISCLOSURE

In an aspect of the disclosure, a delivery sleeve comprises: an enclosure having a first portion, an orifice, and a throat disposed between the first portion and the orifice; and a cinching mechanism disposed about the throat, in which the cinching mechanism comprises a plurality of demarcations each of which are indicative of a sized opening of the throat.

The plurality of demarcations comprise symbols, different colors or patterns, each color or pattern of which is indicative of the sized opening of the throat, successive numberings, alphanumerical symbols and/or tactile structures. The plurality of demarcations are disposed at a first end of the cinching mechanism, and the cinching mechanism further comprises a fastener disposed at an end opposite end of the cinching mechanism.

The enclosure comprises a structure that aligns with any of the plurality of demarcations, and in which the structure in combination with any of the plurality of demarcations is indicative of the sized opening of the throat.

In another aspect of the disclosure, a cinching mechanism comprises: a flexible structure comprising a first end and a second end; a plurality of demarcations at the first end of the flexible structure, the plurality of demarcations indicative of a sized opening of a delivery implant sleeve; and a fastening mechanism at the second end of the flexible structure.

In an aspect of the disclosure, a method of using a delivery sleeve comprises: providing the delivery sleeve, the delivery sleeve comprising, an enclosure having a throat with an orifice, and a structure on the delivery sleeve, and a cinching mechanism having a plurality of demarcations, the cinching mechanism disposed about the throat in a loose configuration such that the throat and the orifice are in an open configuration; inserting an implant having a size into the enclosure through the orifice and the throat; and changing the configuration of the throat to a predetermined size opening of the throat corresponding to the size of the implant by aligning one of the plurality of demarcations with the structure.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

FIGS. 12A and 12B depict the cinching mechanism of FIG. 8 used with a delivery sleeve;
FIGS. 13A and 13B depict the cinching mechanism of FIG. 9 used with a delivery sleeve;
FIGS. 14A and 14B depict the cinching mechanism of FIG. 10 used with a delivery sleeve;
FIGS. 16-16C depict additional variations of a belt loop, in addition to showing a designator or frame.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

The following description sets forth certain illustrative examples of the claimed subject matter. Other examples, features, aspects, embodiments, and advantages of the technology should become apparent to those skilled in the art from the following description. Accordingly, the drawings and descriptions should be regarded as illustrative in nature.

Figure 1:
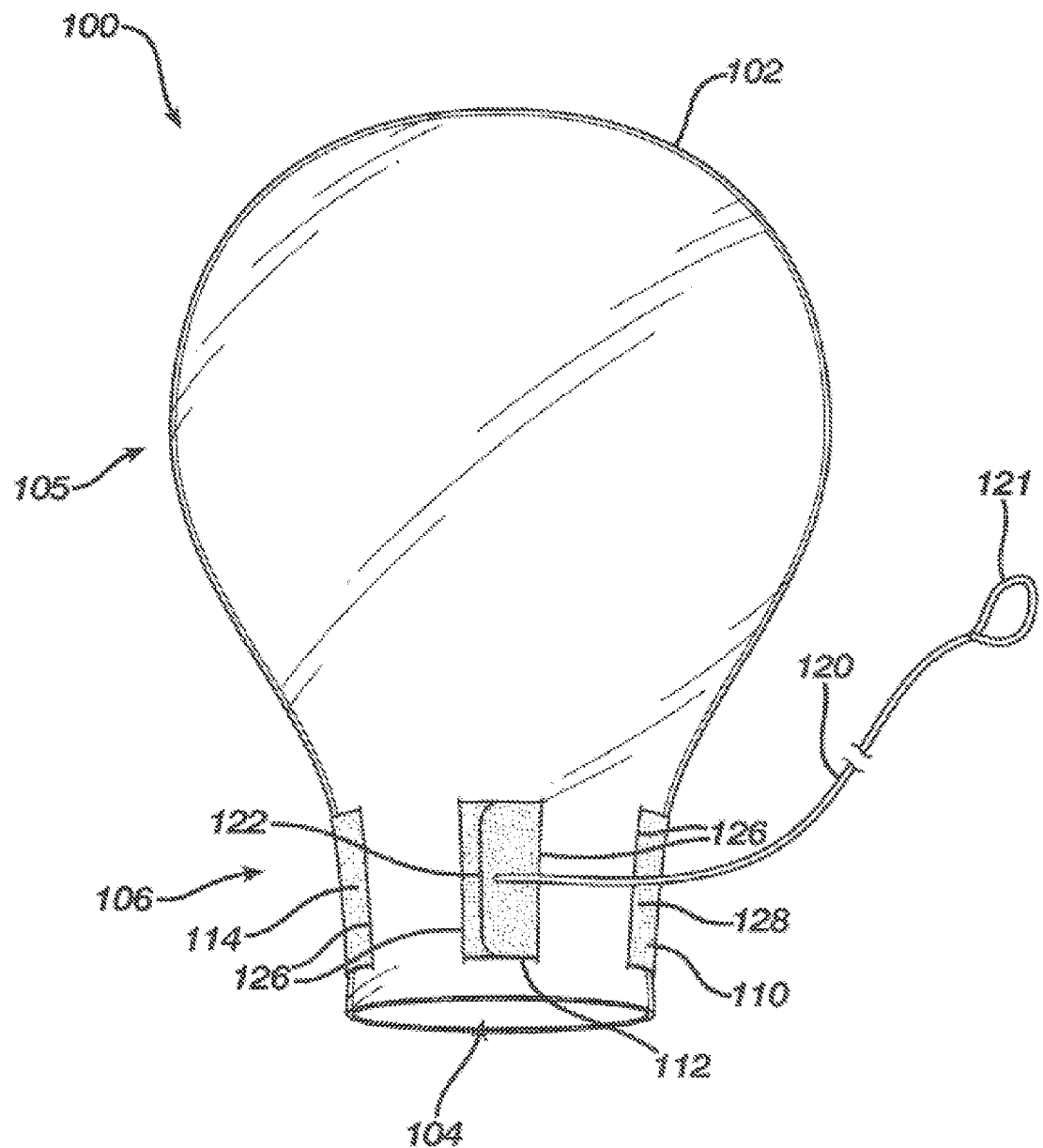
FIG. 1 depicts a delivery sleeve.
Figure 2:
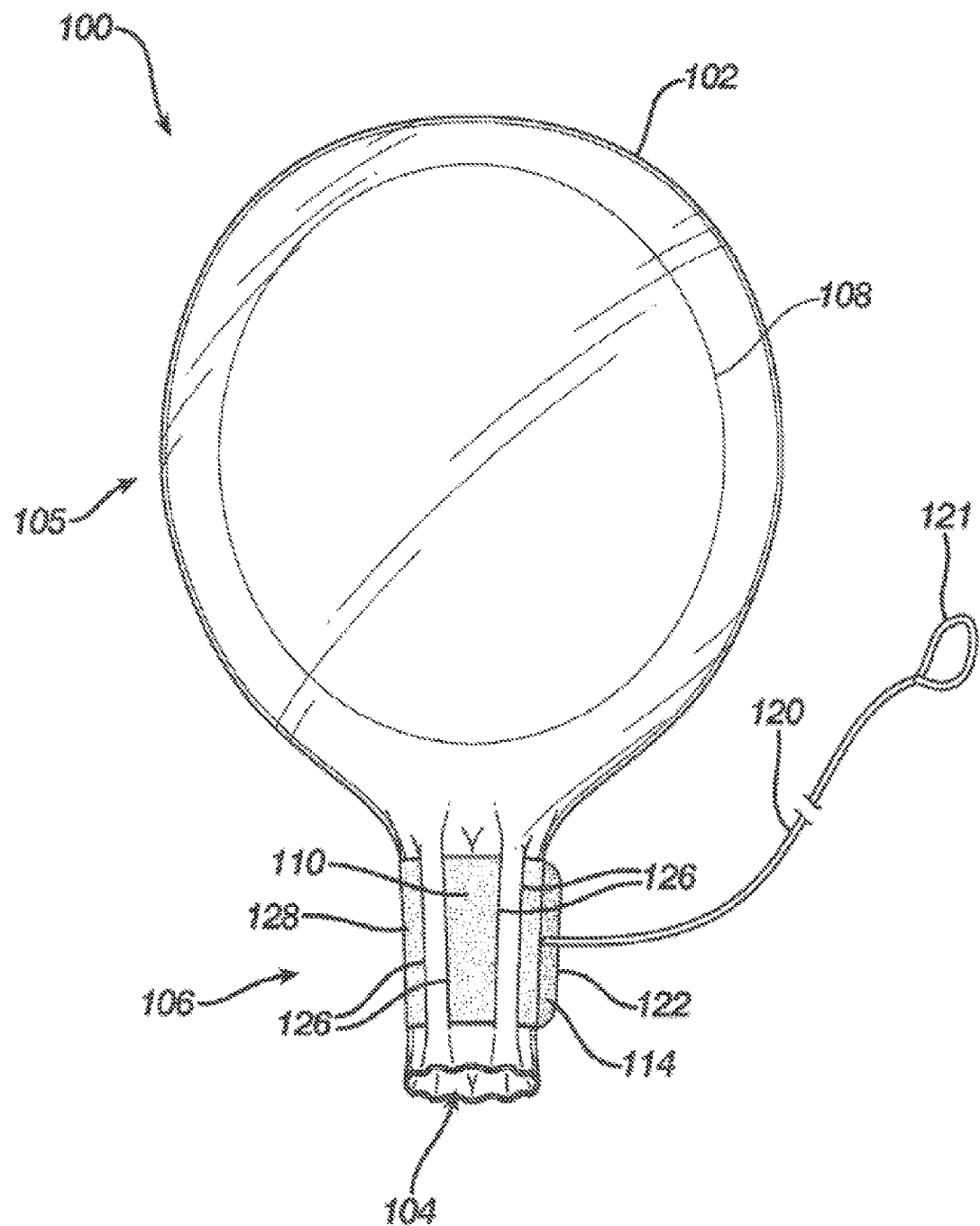
FIG. 2 depicts the delivery sleeve of FIG. 1 in a closed configuration.

FIGS. 1 and 2 show an exemplary embodiment of a delivery sleeve 100. Delivery sleeve 100 may include a thin-walled enclosure 102 with an orifice 104, a bulbous portion 105, and a throat or throat portion 106 connecting bulbous portion 105 to orifice 104. In embodiments, orifice 104 is disposed at an end of throat 106 and may be considered a portion of throat 106. As reflected in FIG. 2, an implant 108, e.g., a silicone-gel implant, may be provided within enclosure 102, typically within bulbous portion 105. Enclosure 102 may be fabricated by any suitable process, e.g., blow molding or sealing two sheets of a suitable material, e.g., vinyl, together to form a seal. In embodiments, throat 106 and orifice 104 each have a diameter or width that is less than a diameter or width of the other portion(s) of enclosure 102, i.e., bulbous portion 105.

Implant 108 may be a breast implant or another type of implant (e.g., biopsy, lumpectomy, calf, buttock, or pectoral). Breast implants typically have a maximum diameter or maximum width ranging from between approximately three inches and eight inches. Implants may be referred to by their maximum width or diameter taken in a plane that is parallel to the base of the implant, e.g., "a five-inch implant." Silicone-gel implants are flexible and pliable, and may be squeezed considerably to constrain the implant in a configuration such that the diameter of the implant may be constricted considerably, e.g., on the order of between approximately two to ten times. For example, if implant 106 is a "three-inch implant" the portion that is three inches may be squeezed to constrict that portion down to a width of, e.g., 1.5 inches. Once the constrictive forces are removed, the portion recovers its original shape having a three-inch diameter.

Bulbous portion 105 may be designed to conform, loosely conform, or loosely surround implant 108, depending on the size. For example, a delivery sleeve 100 may be designed as a delivery sleeve for most or all implant sizes. So designed, bulbous portion 105 may have a maximum width or diameter of between approximately six to eight inches. For example, the maximum width or diameter of bulbous portion 105 may be approximately eight inches. Alternatively, delivery sleeve 100 may be designed as a delivery sleeve for a range of implant sizes, e.g. three- to five-inch implants. In such instances, bulbous portion 105 may have a width or diameter between approximately four to six inches. For example, bulbous portion 105 may have a width or diameter of approximately five inches. Of course, bulbous portion 105 may be provided with smaller diameters, e.g., between approximately one inch and three inches, for other types of and smaller sized implants or with larger diameters, e.g., between approximately eight inches and ten inches, for other types of and larger sized implants. Other types of implants include lumpectomy, biopsy, calf, buttocks, pectoral, etc.

Throat 106 may have a maximum width or diameter that is less than or equal to the width or diameter of bulbous portion 105. As shown in FIG. 1, throat 106 is somewhat narrower than bulbous portion 105. In embodiments, the diameter or width of throat 106 is at least approximately equal to the maximum diameter or width of implant 108, e.g., between approximately three inches and eight inches. Such dimensions may facilitate introducing implant 108 into enclosure 102 because implant 108 need not be compressed and throat 106 need not be stretched to remove interference caused by the throat being narrower than the implant.

The diameter or width of throat 106 is adjustable. A cinching mechanism 110 may be disposed about throat 106, which may be used to adjust the diameter or width of throat 106. In various embodiments, a cinching mechanism may include a flexible structure including a string, filament, tape, strap, band, cable tie, or ribbon, or a combination thereof. In various embodiments, the cinching mechanism may include at least a single band or string, and/or multiple bands or strings. In various embodiments the cinching mechanism may also include a fastener, such as a hook-and-loop type fastener (e.g., VELCRO®), a cord lock (which may be spring loaded), a ratchet (e.g., as in the teeth and pawl of a zip-type cable tie), an elastic ring, or a magnetic ring. The fastener may be used to restrain cinching mechanism 110 in a desired configuration.

As reflected in FIGS. 1 and 2, cinching mechanism 110 comprises a band or cable tie 128 disposed about throat 106 and having a hook-and-loop type fastener 114. In embodiments, cinching mechanism 110 may also comprise a pull cord 120, which may have a loop 121 for a user to pull, connected to an end 122 of band 128. Further, in embodiments, slits, e.g., slits 126 may be disposed through throat 106 and band 128 disposed therethrough such that band 128 may be woven through the slits, akin to a purse string. Alternatively, instead of slits, a sleeve may be disposed about and attached circumferentially to throat 106 such that band 128 may be disposed through the sleeve and about throat 106. Alternatively, instead of a sleeve, a channel may be formed about and circumferentially on throat 106 such that band 128 may be disposed through the channel and about throat 106. Alternatively, eyelets may be affixed circumferentially to throat 106 such that band 128 may be disposed through the eyelets and about throat 106.

An edge 112 of band 128 may be disposed about orifice 104 or may be spaced from orifice 104 by between approximately 0.1 inches and 2 inches. For example, the distance between orifice 104 and edge 112 may be approximately 0.5 inches. In FIG. 1, cinching mechanism 110 is shown in a loose configuration such that orifice 104 is in an open configuration. However, in FIG. 2, cinching mechanism 110 is shown in a cinched configuration such that throat 106 and orifice 104 are in a closed configuration. The hook-and-loop fastener 114 is fastened such that cinching mechanism 110 is maintained in the cinched configuration and throat 106 and orifice 104 are maintained in the closed configuration. Further details of cinching mechanism is discussed with respect to FIGS. 8-11.

In FIG. 2, throat 106 and orifice 104 are maintained in a closed configuration such that throat 106 has a cylindrical or approximately cylindrical shape. Notably, the diameter or width of throat 106 is substantially less than it was in the open configuration of FIG. 1, and it is also substantially less than the diameter or width of bulbous portion 105, which contains implant 108. Thus, throat 106 and orifice 104 may have a width or diameter that approximates a width of an incision through which implant 108 is to be inserted into a subject. Alternatively, the width or diameter of throat 106 and orifice 104 in the closed configuration may be between approximately one quarter to three quarters of the maximum width or diameter of implant 108. Because breast implants typically have a maximum width or diameter between approximately three inches and eight inches, throat 106 may have a width or diameter in the closed configuration between approximately 0.75 inches (i.e., one quarter of three inches) and six inches (i.e., three quarters of eight inches). For example, if implant 108 is a five-inch implant, the width or diameter of throat 106 in the closed configuration may be between approximately 1.2 inches and 3.8 inches. Although the width or diameter of throat 106 in the closed configuration has been provided based upon typical breast-implant sizes, it should be understood that delivery sleeve 100 may be used to deliver other types of implants (e.g., lumpectomy, biopsy, calf, buttocks and pectoral implants). Accordingly, the width or diameter of throat 106 in the closed configuration may also be between approximately 0.2 inches and 0.8 inches or between approximately six inches and eight inches. In embodiments, band 128 may include graphical representations, e.g., indicators or markings that are symbolic or numeric, indicating the size of orifice 104 and/or throat 106 in the closed configuration, or the size of the implant to be introduced, as further described with respect to FIGS. 8-11. Because throat 106 may have a diameter or width in the closed configuration that is less than a width of an incision through which implant 108 will pass, such incisions typically ranging from approximately two inches to approximately five inches, opening 104 and a portion of throat 106 may be inserted through the incision with relative ease, minimal trauma, and minimal contact with tissues surrounding the incision.

A manufacturer of sleeve 100 may provide a sterilized and packaged product that includes enclosure 102 with implant 108 disposed therein. For example, the manufacturer may insert implant 108 into enclosure 102 through orifice 104 and throat 106 while they are in an open configuration, and then cinch cinching mechanism 110 and fasten fastener 114 to change the configuration of orifice 104 and throat 106 to a closed configuration. Alternatively, a manufacturer of sleeve 100 may provide a sterilized and packaged product that includes enclosure 102 but excludes implant 108 such that a medical professional, e.g., surgeon, would provide implant 108 and insert implant 108 into enclosure 102 through orifice 104 and throat 106, and then cinch cinching mechanism 110 herself.

After implant 108 is disposed within enclosure 102 and after cinching mechanism 110 has been cinched to place throat 106 and orifice 104 into the closed configuration, orifice 104 and a portion of throat 106 may be passed through an incision and into a tissue pocket, e.g., a breast pocket, of a subject, such as a human female patient. Once the medical professional has positioned orifice 104 at a desired location, she may squeeze enclosure 102 about implant 108 to force or extrude implant 108 through throat 106 and out of orifice 104 into the tissue pocket. The medical professional may then remove throat 106 and orifice 104 from the tissue pocket through the incision, leaving implant 108 behind. In some variations, before forcing or extruding the implant through throat 106, the medical professional may release fastener 114, e.g., by pulling on end 122. In those embodiments that include pull cord 120, this action may be facilitated by pulling on pull cord 120, e.g., by pulling on loop 121. Once unfastened, such that cinching mechanism 110 is no longer in the cinched configuration, and throat 106 and orifice 104 are no longer constrained in the closed configuration, implant 108 may be passed into the tissue pocket, through throat 106 and orifice 104, by squeezing enclosure 102, perhaps with less force than if throat 106 remained in the cinched configuration. Either way, after implant 108 is disposed in the tissue pocket, the medical professional may remove throat 106 and orifice 104 from the tissue pocket through the incision, leaving implant 108 behind.

As shown, orifice 104 is a single orifice, however, in embodiments, additional orifices may be included elsewhere on enclosure 102. In embodiments (not shown) a second orifice may be included opposite orifice 104. This second orifice may be sized to permit insertion of implant 108 into enclosure 102, e.g., without deforming implant 108. Moreover, in embodiments, the second orifice, when fully opened, may be the same size, smaller than, or larger than the opposite orifice 104 when fully opened. In embodiments (not shown), enclosure 102 may not have the bulbous form reflected in the figures. Rather, it may have a tapered (e.g., frustoconical) form. In these tapered embodiments, the width of enclosure 102 is largest at the end opposite orifice 104 and is smallest at the end including opening 104.

Figure 3:
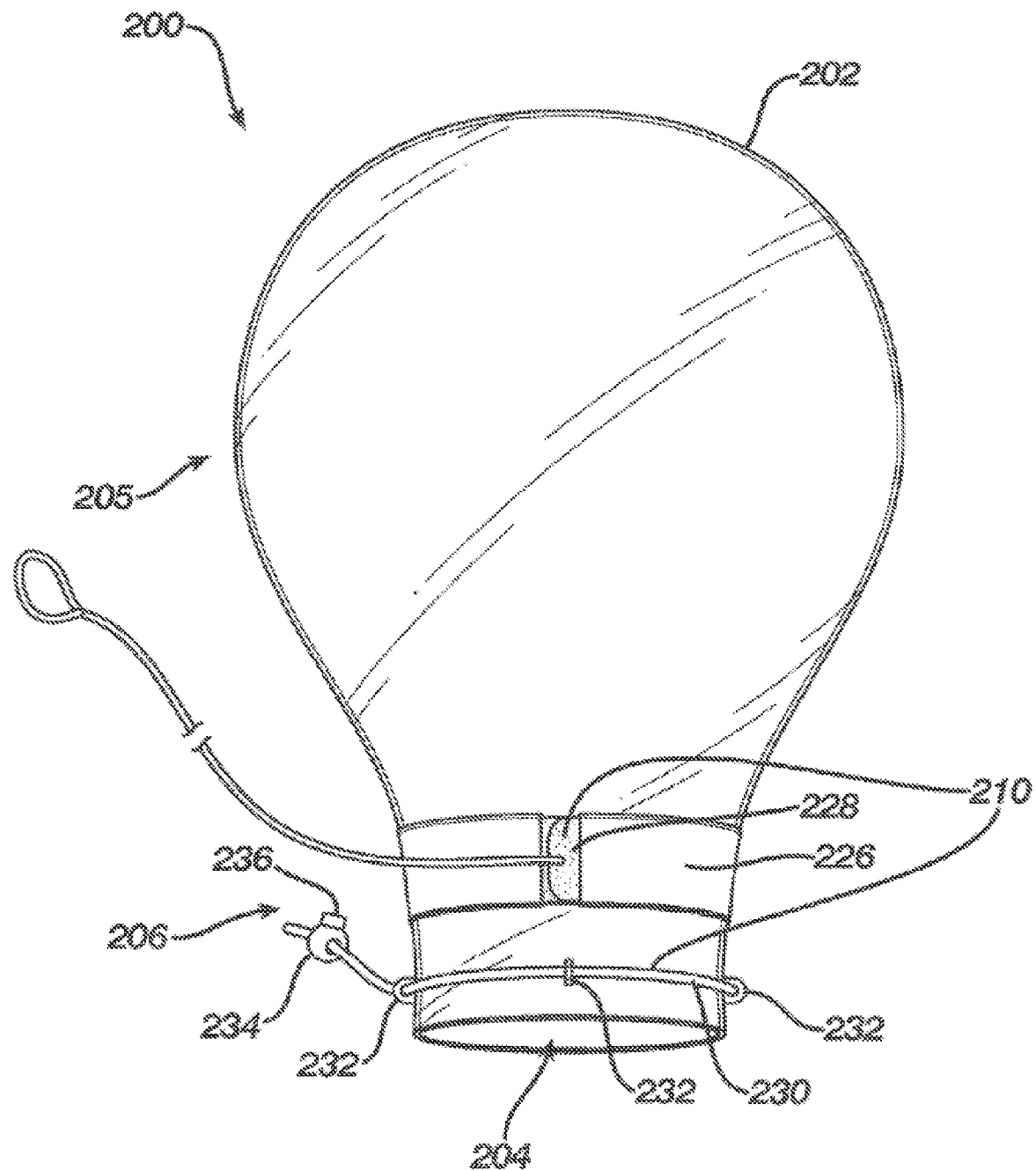
FIG. 3 depicts a first alternate embodiment of a delivery sleeve.
Figure 4:
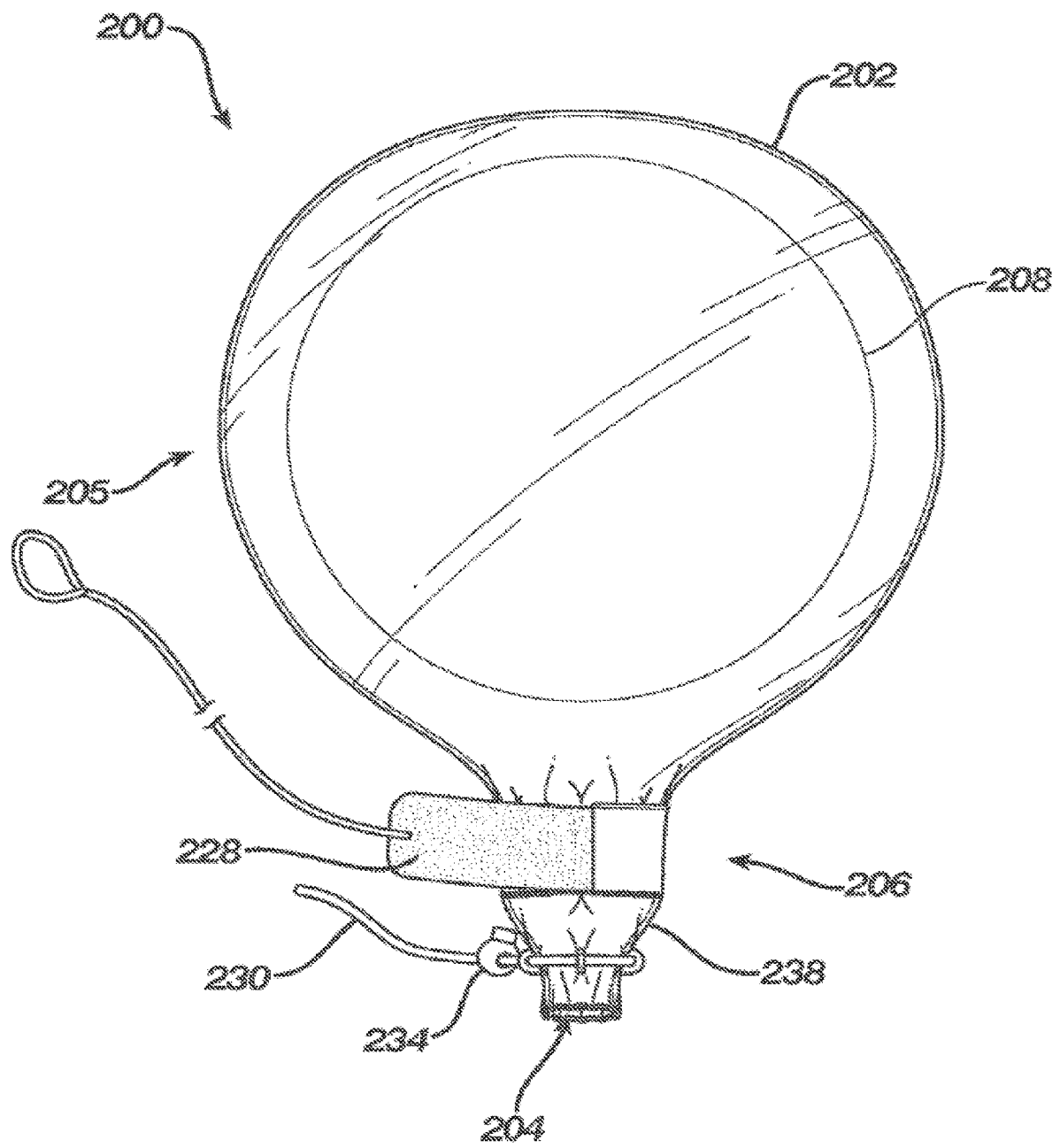
FIG. 4 depicts the delivery sleeve of FIG. 3 in a closed configuration.

FIGS. 3 and 4 show an alternate embodiment of a delivery sleeve. Delivery sleeve 200 includes an enclosure 202 comprising a cinching mechanism 210 that includes a band 228 disposed about throat 206 through a sleeve 226 that is disposed circumferentially around throat 206, adjacent to bulbous portion 205. Cinching mechanism 210 also includes a string 230 disposed about orifice 204 through eyelets 232, which are circumferentially attached to throat 206 adjacent to orifice 204. Band 228 may include a fastener 214, e.g., a hook-and-loop type fastener. String 230 may also include a fastener, e.g., fastener 234, which may be a cord lock having a release button 236. Band 228 and string 230 enable placing throat 206 and orifice 204 into a closed configuration having a conical shape. That is, string 230 may be constricted about orifice 204 more than band 228 may be constricted about throat 206 such that the diameter or width of orifice 204 is smaller than the diameter or width of throat 206. Thus, in the closed configuration (e.g., FIG. 4) the diameter or width of throat 206 may be between approximately 0.75 inches and six inches whereas the diameter or width of orifice 204 may be between approximately 0.5 inches and 5.5 inches while also being smaller than the diameter or width of throat 206 in the closed configuration. For example, in the closed configuration, the diameter of throat 206 may be approximately two inches and the diameter orifice 204 may be one inch, thus creating a tip 238 of enclosure 200 having a conical shape. Further, in the closed configuration, band 228 and string 230 provide substantial mass to tip 238, thereby providing tip 238 with the ability to resist some deformation and facilitate introduction of tip 238 through an incision.

Figure 18A:
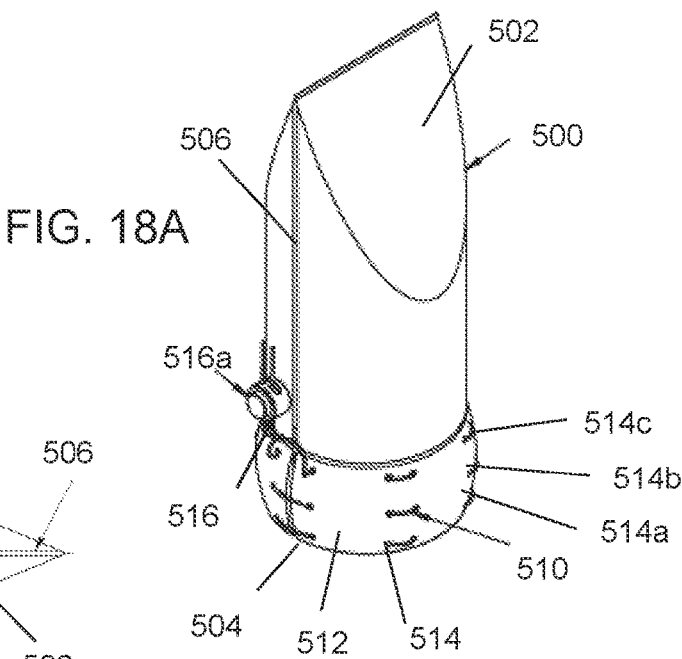
FIGS. 18A and 18B depict an alternate delivery sleeve.
Figure 18B:
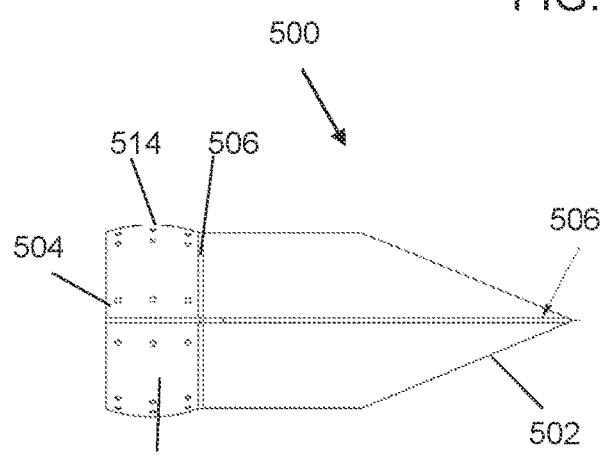

FIGS. 18A and 18B reflect an alternate embodiment of a delivery sleeve 500. Delivery sleeve 500 can be composed of different materials, e.g., LDPE. In FIGS. 18A and 18B, delivery sleeve 500 is shown with a tapered top section 502 and a conical opening or orifice 504. Seams 506 are shown along a length of the delivery sleeve 500 and about a throat 512. Seams 506 can be a heat seal used to assemble opposing halves of delivery sleeve 500, and throat 512 about the assembled halves of delivery sleeve 500. An interior of delivery sleeve 500 can be coated with a hydrophilic coating; although other coatings are also contemplated herein.

In FIG. 18A, delivery sleeve 500 is shown with cinching mechanism 510 in a loose configuration. Cinching mechanism 510 is disposed about throat 512 though a plurality of holes 514. In this embodiment, cinching mechanism 510 may include a string (or a band) disposed about throat 512 though a plurality of holes 514. In more specific embodiments, cinching mechanism 510 may include a cord composed of PTFE material; although other materials are contemplated herein. In FIG. 18B, delivery sleeve 500 is shown without cinching mechanism 510 to show the plurality of holes 514 in throat 512.

In FIG. 18A, cinching mechanism 510 is disposed about throat 512 several times; that is, as shown, cinching mechanism 510 has multiple convolutions, e.g., first convolution 514a, second convolution 514b, and third convolution 514c. Although this embodiment is shown as having three convolutions, it should be understood that greater or fewer convolutions would also enable delivery sleeve to be cinched into a closed configuration. For example, even an incomplete convolution (e.g., 270 degrees) would permit for a closed configuration of throat 512.

Cinching mechanism 510 may include a fastener, e.g., fastener 516, which may be a cord lock having a release button 516a. Fastener 516 enables placing cinching mechanism 510 abut throat 512 and orifice 504 into a closed configuration having a conical shape. That is, cinching mechanism 510 may be constricted about orifice 504 such that the diameter or width of orifice 204 becomes smaller.

Figure 5:
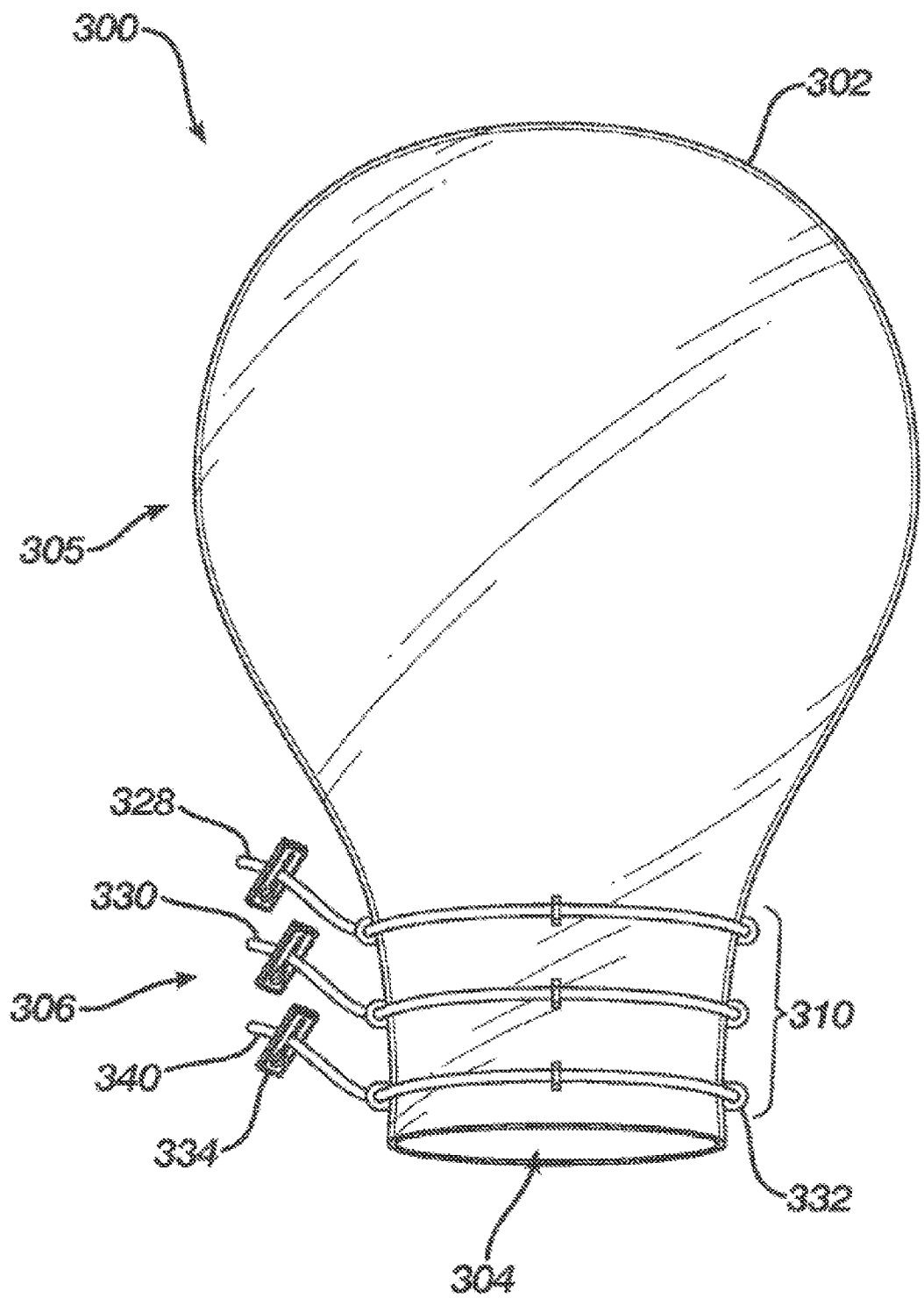
FIG. 5 depicts another a second alternative embodiment of a delivery sleeve.

As noted above, in various embodiments, the cinching mechanism may include at least a single band or string, and/or multiple bands or strings. For example, FIG. 5 reflects a delivery sleeve 300 with a cinching mechanism 310 in a loose configuration. Cinching mechanism 310 includes a first string 328, a second string 330, and a third string 340 disposed about throat 306, through eyelets 332, with string 340 disposed adjacent to orifice 304. Alternatively, strings 328, 330, and 340 may be contained within a sleeve about opening 304. Cinching mechanism 310, may also include a slide clamps 334 disposed on at least one of the strings, which may be used to maintain the strings in a constricted or closed configuration. String 340 may be constricted more than string 330, which may be constricted more than string 328. Accordingly, in the closed configuration, tip 340 may have a conical shape imparted by strings 328, 330, and 340. Alternatively, strings 328, 330, and 340 may be constricted by the same or approximately the same amount to impart a cylindrical shape to throat 306.

Figure 6:
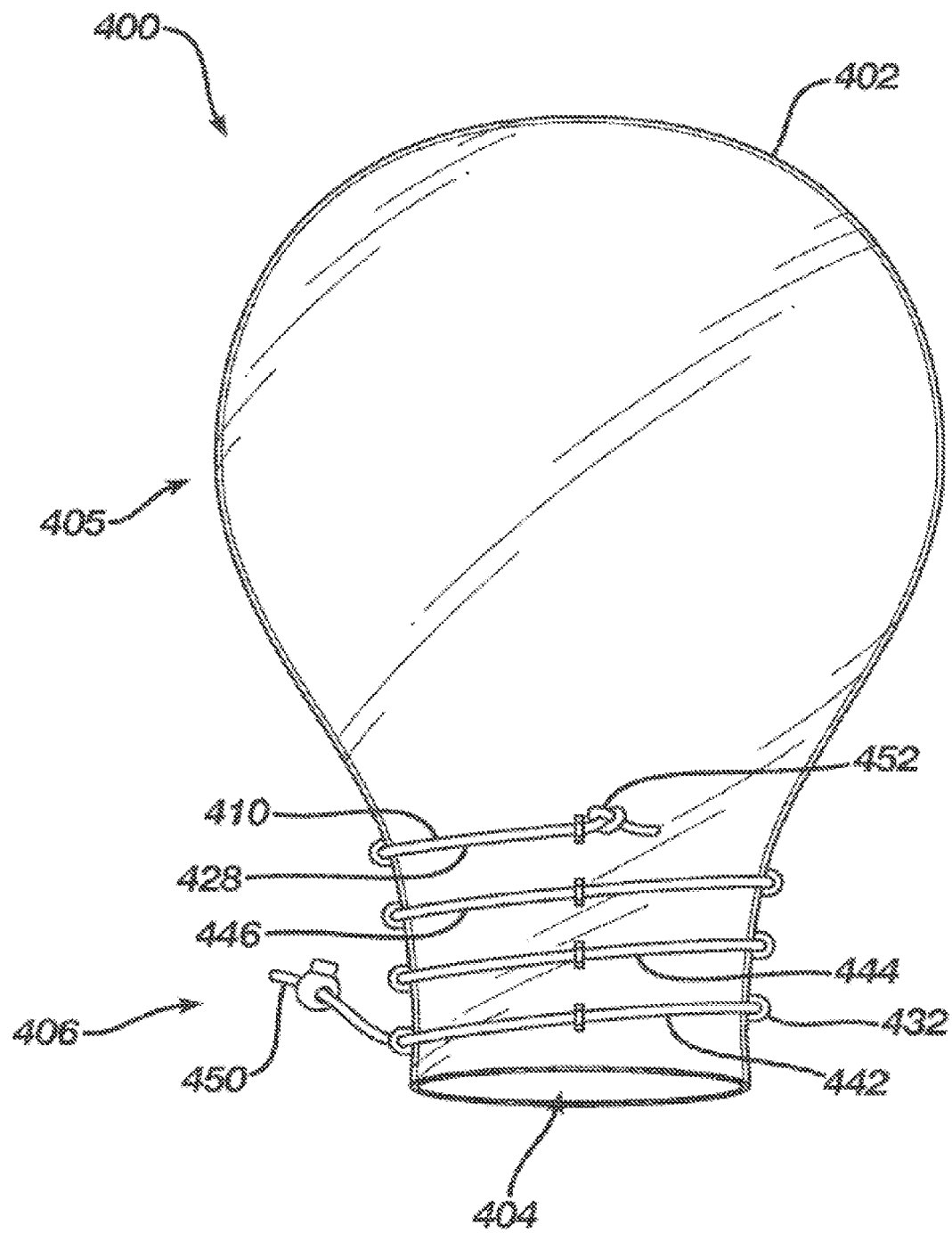
FIG. 6 depicts a third alternative embodiment of a delivery sleeve.
Figure 7:
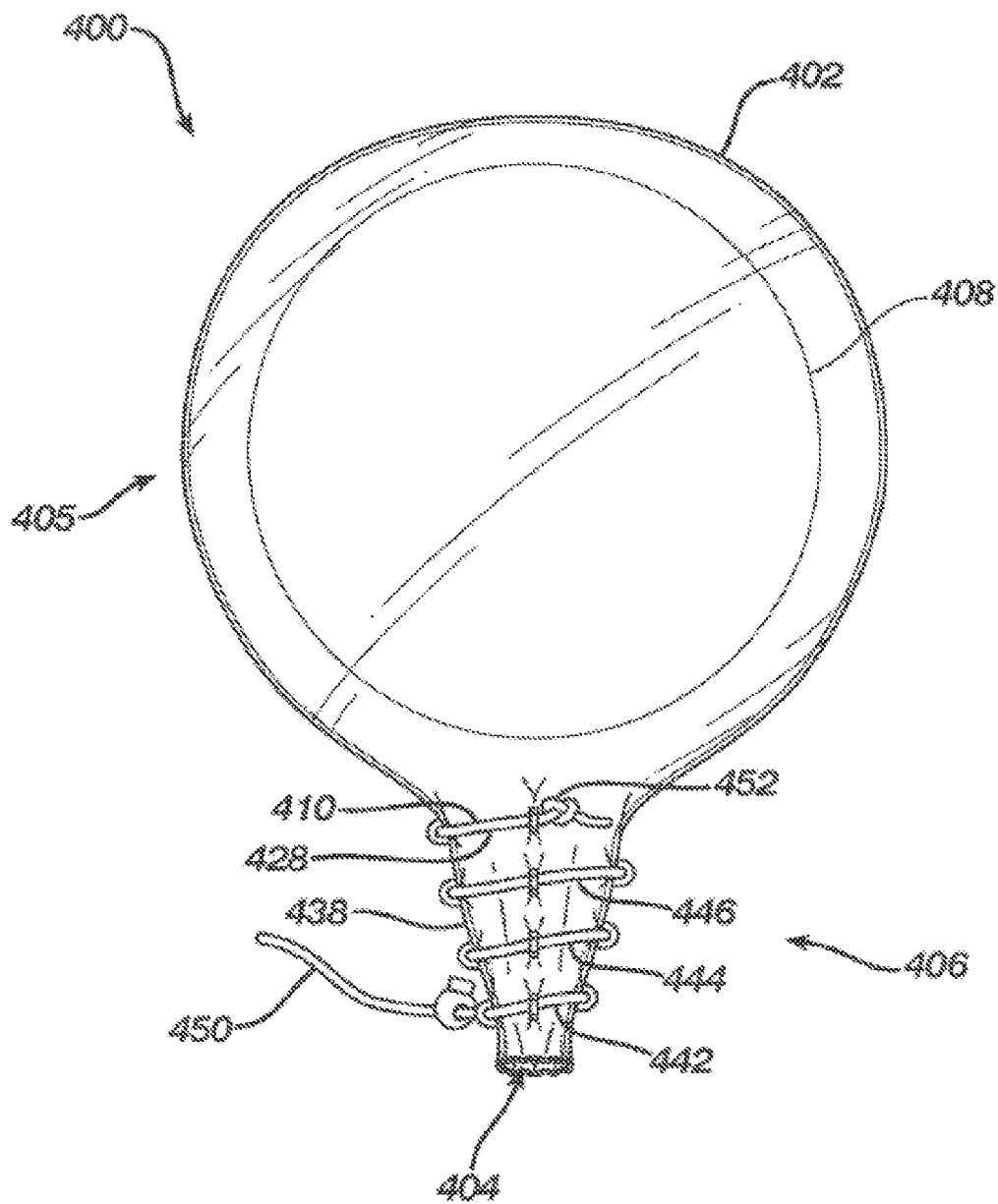
FIG. 7 depicts the delivery sleeve of FIG. 6 in a closed configuration.

FIGS. 6 and 7 reflect an alternate embodiment of a delivery sleeve. In FIG. 6, delivery sleeve 400 is shown with cinching mechanism 410 in a loose configuration. In FIG. 7 delivery sleeve 400 is shown with cinching mechanism 410 in a cinched configuration. In this embodiment, cinching mechanism 410 may include a string 428 (or a band) disposed about throat 410 though eyelets 432 along an angled or helical path. As shown, string 428 has multiple convolutions, e.g., first convolution 442, second convolution 444, and third convolution 446. At least a portion of first convolution 442 is disposed adjacent to orifice 404. First convolution 442 may further include a first end 450 of string 428. Third convolution 446 may include a second end 452 that is fixedly attached to throat 406, e.g., by ultrasonic welding, or by providing a bead or knot larger than a hole in eyelet 432 such that the bead or knot cannot pass through eyelet 432. By displacing first end 450 away from orifice 404, e.g., by pulling on it, first convolution 442 will reduce in diameter by a greater amount than second convolution 444, which will reduce in diameter by a greater amount than third convolution 446. Accordingly, tip 438 will have a conical shape when throat 206 is placed in the closed configuration shown in FIG. 7. Although this embodiment is shown as having three convolutions, it should be understood that greater or fewer convolutions would also enable placing tip 438 into a conical shape in the closed configuration. For example, even an incomplete convolution (e.g., 270 degrees) would permit for a closed configuration of throat 406 having a tip 438 with a conical shape.

In some embodiments, a lubricant can be dispersed inside the enclosure (e.g., 102) prior to implant delivery. Optionally, in some embodiments, a lubricant coating can be used on inner surface of the enclosure. Such lubricants typically comprise one or more of the following substances: saline, glycerin, hydroxyethyl cellulose, Polyethylene glycol (PEG), propylene glycol (propane-1,2-diol), and carbomer. Suitable commercially available lubricants include, e.g., HR® Lubricating Jelly and McKesson Lubricating Jelly. These lubricants can be provided into the enclosure as a liquid or fluid; or alternatively as semi-liquid or paste; or alternatively as dry powders and/or dry coatings which are activated by water. Optionally, in some embodiments, a lubricious or low-friction material can be used to form the enclosure or at least coat an inner surface of the enclosure. Such coatings can comprise low-friction hydrophilic and/or hydrophobic coatings comprised of, e.g., PTFE/fluorocarbons, hydrogels, polymethacrylates; polyvinylpyrrolidone (PVP), polyurethane, acrylic polyester, vinyl resin, silicone. Suitable lubricious coatings for medical devices are available from Surmodics, Inc. (Eden Prairie, Minn.) and include their Serene™ lubricious coatings.

FIGS. 8-11 show further details of alternative cinching mechanisms, each of which include different types of demarcations, e.g., numbers, symbols, colors, tactile feel, etc. For example, in each of the alternative embodiments, the cinching mechanism includes demarcations (indicators) that, relative to the implant introducing device (e.g., implant delivery sleeve), provide a user with an indication of the size of the resulting opening of throat 106. Specifically, the cinching mechanism can be adjusted such that the demarcations are moved into alignment with a structure on the implant delivery sleeve, e.g., slits 126 shown in FIG. 1, eyelets 232 shown in FIG. 3, eyelets 332 shown in FIG. 5, etc., to indicate different sized openings of throat 106 or a size of an implant to be inserted within the implant introducing device. In this way, when adjusting the opening of an implant introducer, e.g., breast implant introducer, it is now possible to ensure that the adjusted opening of throat 106 is compatible for the size implant being considered.

Figure 8:
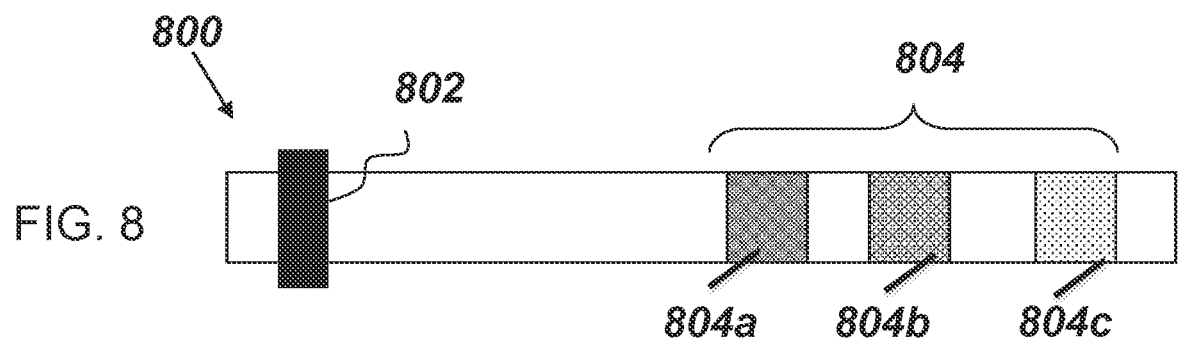
FIG. 8 depicts an alternative cinching mechanism with demarcations.

More specifically, as shown in FIG. 8, cinching mechanism 800 may include a string, filament, tape, strap, band, cable tie, pull cord or ribbon, or a combination thereof. An optional fastener 802 is provided at one end of the cinching mechanism 800 and demarcations 804 are provided at another end, e.g., opposite end, of the cinching mechanism 800. As described with respect to FIGS. 2, 3, and 5, for example, the fastener 802 can include a hook-and-loop type fastener (FIG. 2), a cord lock having a release button (FIG. 3) or slide clamps (FIG. 5); although other fasteners are contemplated herein such as a cord lock (which may be spring loaded), a ratchet (e.g., as in the teeth and pawl of a zip-type cable tie), an elastic ring, or a magnetic ring to name a few additional fasteners.

Still referring to FIG. 8, the demarcations 804 comprise different colors or different tactile configurations, e.g., bumps, etc., each of which are representative of a sized opening of throat 106 and, in embodiments, a size of the implant being inserted into the implant introducing device. As discussed in more detail with respect to FIGS. 12A and 12B, the demarcations 804 can be differently colored bands 804a, 804b, 804c, corresponding to different sizes. In an alternative embodiment, demarcations 804a, 804b, 804c can be different saturations or hues of colors, e.g., dark color, intermediate or lighter hue or saturation of the same color, etc., corresponding to different sizes. In another alternative embodiment, demarcations 804a, 804b, 804c can be different patterns of colors, corresponding to different sizes. These different colors or different tactile configurations 804 are aligned with a structure of the implant introducing device to indicate different sized openings of throat or size implant being considered.

Figure 9:
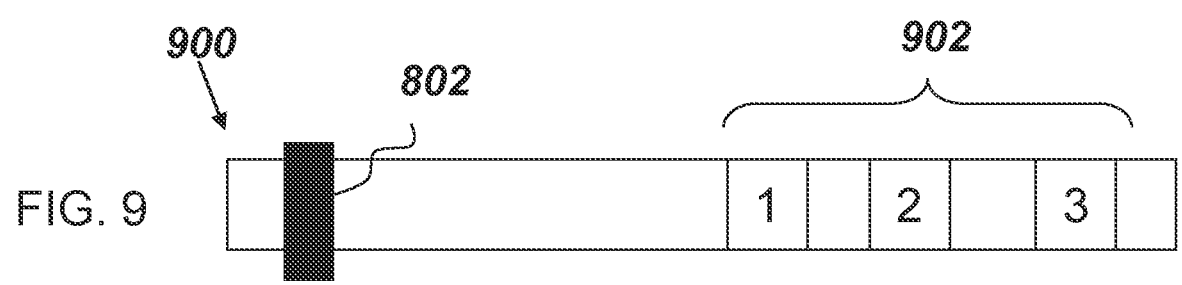
FIG. 9 depicts another alternative cinching mechanism with demarcations.

FIG. 9 shows cinching mechanism 900 which comprises a string, filament, tape, strap, band, cable tie, pull cord or ribbon, or a combination thereof. The cinching mechanism 900 also includes the optional fastener 802 and demarcations 902. In this embodiment, the demarcations 902 comprise different numbers, each of which are representative of a sized opening of throat 106 and, in embodiments, a sized opening compatible for the size implant being considered for insertion into the enclosure. In alternate embodiments, the demarcations 902 can be alphanumeric, alphabetical, etc., also representative of a sized opening of throat 106 and/or the sized opening compatible for the size implant being considered, e.g., the size of the implant to be inserted within the enclosure.

Figure 10:
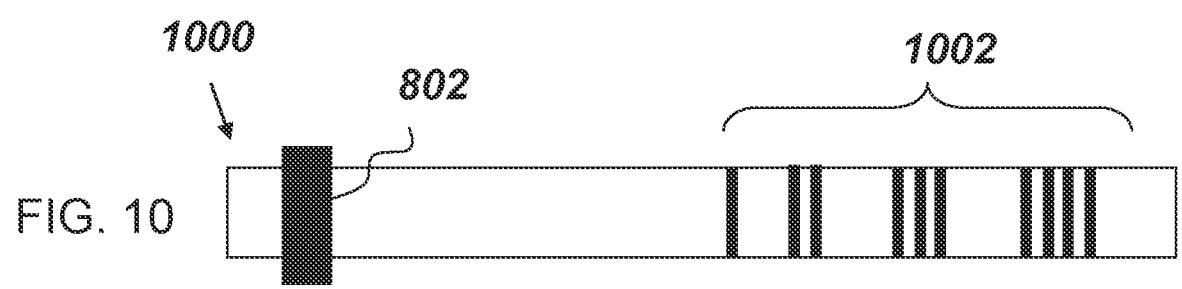
FIG. 10 depicts another alternative cinching mechanism with demarcations.

FIG. 10 shows cinching mechanism 1000, which again comprises a string, filament, tape, strap, band, cable tie, pull cord or ribbon, or a combination thereof. The cinching mechanism 1000 includes the optional fastener 802 and demarcations 1002. In this embodiment, the demarcations 1002 comprise different symbols, each of which are representative of a sized opening of throat 106 and, in embodiments, a sized opening compatible for the size implant being considered for insertion into the enclosure. For example, the symbols 1002 include lines that are successively increased in number, e.g., one line, two lines, three lines, etc.

Figure 11:
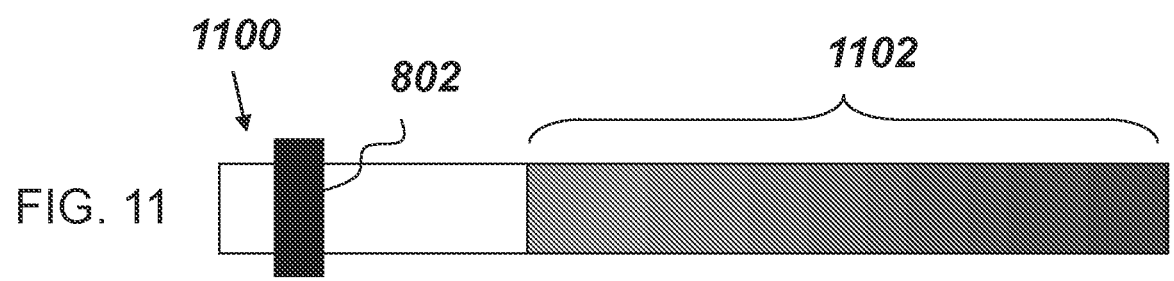
FIG. 11 depicts another alternative cinching mechanism with demarcations.

FIG. 11 shows cinching mechanism 1100, which again comprises a string, filament, tape, strap, band, cable tie, pull cord or ribbon, or a combination thereof. The cinching mechanism 1100 also includes the optional fastener 802 and demarcations 1102. The demarcations 1102 comprise various colors in a continuous stripe, in which each color may be representative of a sized opening of throat 106 and, in embodiments, the sized opening compatible for the size implant being considered for insertion into the enclosure. In alternative embodiments, each color could represent an implant size range for the diameter of the opening, in which the user would pull the strap until the fastener is within the desired color range.

Figure 15A:
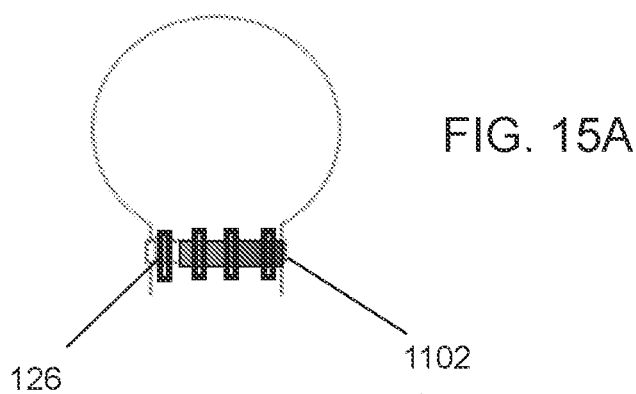
FIGS. 15A and 15B depict the cinching mechanism of FIG. 11 used with a delivery sleeve.
Figure 15B:
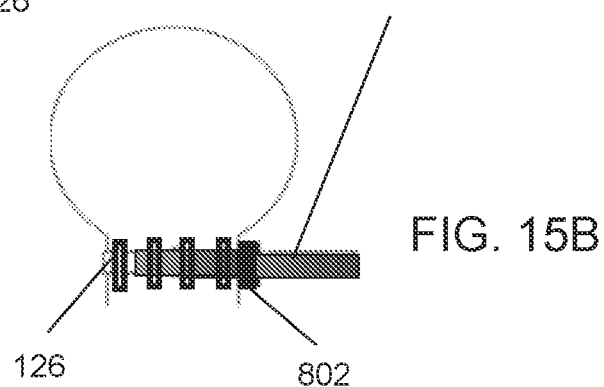

By virtue of the embodiments illustrated and described herein, Applicant has devised a method and variations thereof for closing or cinching of an implant introducing sleeve with differently sized openings as shown, for example, in FIGS. 12A-15B. More specifically, FIGS. 12A and 12B show the use of the cinching mechanism 800 of FIG. 8, FIGS. 13A and 13B show the use of the cinching mechanism 900 of FIG. 9, FIGS. 14A and 14B show the use of the cinching mechanism 1000 of FIG. 10, and FIGS. 15A and 15B show the use of the cinching mechanism 1100 of FIG. 11. In each of these embodiments, the user pulls on the cinching mechanism until a desired demarcation 804, 902, 1002 aligns with a structure, e.g., slit 126, of the implant introducing sleeve. For example, FIGS. 12B, 13B, 14B, 15B show a smaller opening of the implant introducing device 100 compared to FIGS. 12A, 13A, 14A, 15A, respectively. The opening becomes smaller by the user pulling on the cinching mechanism 800 until a desired demarcation (indicative of a certain size) 804, 902, 1002, 1102 aligns with the structure, e.g., slit 126.

Referring to FIGS. 12B, 13B, 14B, 15B optional fastener 802 is shown relative to demarcations 804, 902, 1002 on cinching mechanism 800, 900, 1000, 1100, which comprises a string, filament, tape, strap, band, cable tie, pull cord or ribbon, or a combination thereof. In some embodiments, proximity to fastener 802 and visibility immediately after fastener 802, indicates the size to which the cinching mechanism is opened or closed. Fastener 802 represents a structure defining the size of cinching in combination with demarcations 804, 902, 1002, 1102. FIG. 12B shows the cinching mechanism open to size corresponding to demarcation 804a. FIG. 13B shows the cinching mechanism open to size corresponding to demarcation "1" as opposed to demarcations "2", "3". FIG. 14B shows the cinching mechanism open to size corresponding to demarcation "I" as opposed to demarcations "II", "III". FIG. 15B shows the cinching mechanism open to size corresponding to a different shading.

By way of more specific example, and referring to FIGS. 12A and 12B, demarcations 804, in some embodiments, are differently colored bands 804a, 804b, 804c, optionally of the same width and shape, but different in color or pattern. In one embodiment, demarcation 804a is colored red and corresponds to size 1, demarcation 804b is colored yellow and corresponds to size 2, and demarcation 804c is colored green and corresponds to size 3. In an alternative embodiment, demarcation 804a is colored solid dark color (such as black) and corresponds to size 1, demarcation 804b is colored intermediate or lighter hue or saturation of the same color (such as colored dark grey) and corresponds to size 2, and demarcation 804c is colored very light hue or saturation of the same color (such as colored light grey) and corresponds to size 3. In yet another alternative embodiment, demarcation 804a is patterned solid dark color (such as black) and corresponds to size 1, demarcation 804b is patterned with dense black dots (or crosshatch) patterning and corresponds to size 2, and demarcation 804c is colored with low density black dots (or crosshatch) and corresponds to size 3.

In some embodiments, certain slits (or in some embodiments belt loops) 126 are structured as designated structure for identification of the demarcations 804 defining specific sizes. As shown in FIG. 12A, slits or belt loops 126a and 126b define between them a position where the colored demarcation 804 is viewable when aligned and thus defining the size to which the cinching mechanism is open or closed, where the size is associated with given demarcation. For example, as shown in FIG. 12A, colored or patterned band of demarcation 804a is aligned between slits or belt loops 126a and 126b, said demarcation 804a viewable between slits or belt loops 126a and 126b and indicating that cinching mechanism is prepared for corresponding or desirable implant size, throat size, and or tissue pocket size.

Figures 16A, 16B, 16C:
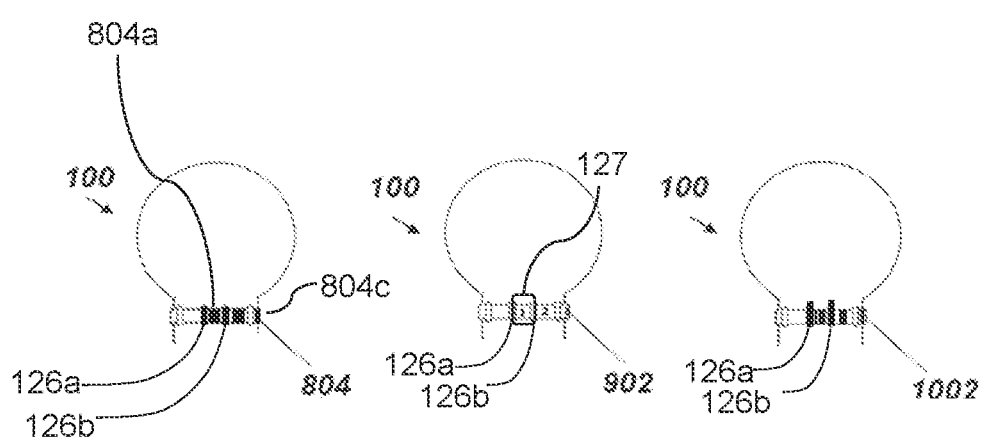

FIGS. 16A-16C show additional variations of the belt loop 126a, 126b, 126b, in addition to showing a designator 127. For example, in some embodiments, indicating slits or belt loops 126a and 126b between which demarcation 804 should be observed for ascertaining the cinching size, are designated by coloring or by markings to indicate to the user the zone where the demarcation 804 should be observed. Referring to FIG. 16A, slits or belt loops 126a and 126b are colored differently than other slits or belt loops 126. Referring to FIG. 16B, slits or belt loops 126a and 126b are indicated by a designator or frame 127, such as a frame around slits or belt loops 126a and 126b or around space between slits or belt loops 126a and 126b. Referring to FIG.

16C, slits or belt loops 126a and 126b are sized differently (are larger) than other slits or belt loops 126.

Figure 17A:
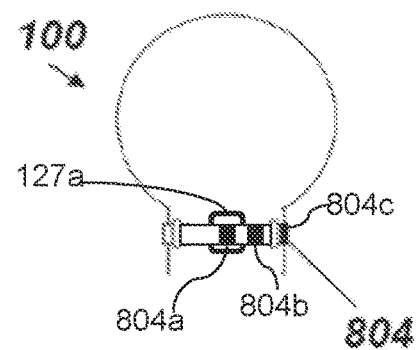
FIGS. 17A and 17B depict the cinching mechanism of FIG. 10 used with a delivery sleeve.
Figure 17B:
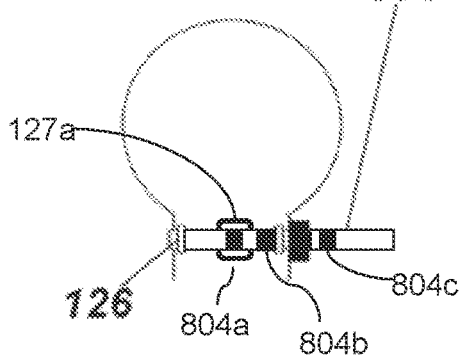

Referring to FIGS. 17A, 17B, in some embodiments, frame 127a or similar structure can be drawn on the surface of delivery sleeve 100 and configured for designating area of alignment with demarcations 804 with corresponding demarcation 804 can be observed to align with frame 127a for ascertaining the cinching size. Referring to FIGS. 17A, 17B, clearly shown is position where the colored demarcation 804 is viewable when aligned with frame 127b and thus defining the size to which the cinching mechanism is open or closed, said size associated with the given demarcation. As shown in FIGS. 17A, 17B, colored or patterned band of demarcation 804a is aligned within frame 127a, said demarcation 804a viewable within frame 127a indicating that cinching mechanism is prepared for corresponding or desirable implant size, throat size, and or tissue pocket size. Similarly to demarcations 804 in FIGS. 17A, 167, demarcations 902, 1002 (not shown) can be configured for corresponding alignment with frame 127a or similar structure that can be drawn on the surface of delivery sleeve 100 designating area of alignment with demarcations 902, 1002.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A delivery sleeve, comprising:
an enclosure having a first portion, an orifice, and a throat disposed between the first portion and the orifice; and
a cinching mechanism disposed about the throat,
in which the cinching mechanism comprises a plurality of demarcations each of which are indicative of a sized opening of the throat.

2. The delivery sleeve of claim 1, in which the plurality of demarcations comprise symbols.

3. The delivery sleeve of claim 2, in which the symbols comprise lines.

4. The delivery sleeve of claim 1, in which the plurality of demarcations comprise different colors or patterns, each color or pattern of which is indicative of the sized opening of the throat.

5. The delivery sleeve of claim 1, in which the plurality of demarcations comprise successive numberings.

6. The delivery sleeve of claim 1, in which the plurality of demarcations comprise alphanumerical symbols.

7. The delivery sleeve of claim 1, in which the plurality of demarcations comprise tactile structures.

8. The delivery sleeve of claim 1, in which the enclosure comprises s a structure that aligns with any of the plurality of demarcations, and in which the structure in combination with any of the plurality of demarcations is indicative of the sized opening of the throat.

9. The delivery sleeve of claim 8, in which the structure comprises slits or eyelets or a fastener.

10. The delivery sleeve of claim 1, in which the cinching mechanism includes a string, filament, tape, strap, band, cable tie, ribbon, or a combination thereof.

11. The delivery sleeve of claim 10, in which the plurality of demarcations are disposed at a first end of the cinching mechanism, and the cinching mechanism further comprises a fastener disposed at an end opposite end of the cinching mechanism.

12. The delivery sleeve of claim 11, in which the fastener includes a hook-and-loop fastener, a cord lock, a ratchet, an elastic ring, a magnetic ring, or a combination thereof.

13. The delivery sleeve of claim 11, in which the fastener comprises a releasable fastener.

14. A cinching mechanism, comprising:
a flexible structure comprising a first end and a second end;
a plurality of demarcations at the first end of the flexible structure, the plurality of demarcations indicative of a sized opening of a delivery implant sleeve; and
a fastening mechanism at the second end of the flexible structure.

15. The cinching mechanism sleeve of claim 14, in which the plurality of demarcations comprise symbols, different colors, successive numberings, tactile configurations, or alphanumerical symbols.

16. The cinching mechanism of claim 14, in which the flexible structure includes a string, filament, tape, strap, band, cable tie, ribbon, or a combination thereof.

17. The cinching mechanism of claim 14, in which the fastening mechanism includes a hook-and-loop fastener, a cord lock, a ratchet, an elastic ring, a magnetic ring, or a combination thereof.

18. The cinching mechanism of claim 17, in which the fastening mechanism comprises a releasable fastener.

19. A method of using a delivery sleeve, comprising:
providing the delivery sleeve, the delivery sleeve comprising,
an enclosure having a throat with an orifice, and
a structure on the delivery sleeve, and
a cinching mechanism having a plurality of demarcations, the cinching mechanism disposed about the throat in a loose configuration such that the throat and the orifice are in an open configuration;
inserting an implant having a size into the enclosure through the orifice and the throat; and
changing the configuration of the throat to a predetermined size opening of the throat corresponding to the size of the implant by aligning one of the plurality of demarcations with the structure.

* * * * *